United States Patent [19]
Olerud

[11] Patent Number: 6,039,740
[45] Date of Patent: Mar. 21, 2000

[54] METHOD AND A DEVICE FOR IMPLANT LOCKING

[76] Inventor: Sven Olerud, Villa Malmen, S-740 11 Länna, Sweden

[21] Appl. No.: 08/908,188

[22] Filed: Aug. 7, 1997

[51] Int. Cl.[7] .................................................. A61B 17/00
[52] U.S. Cl. ................................................................. 606/72
[58] Field of Search .................................. 606/70, 71, 72, 606/73, 60, 61; 411/429, 433, 432, 427, 308, 426

[56] References Cited

U.S. PATENT DOCUMENTS

| | | |
|---|---|---|
| 4,388,921 | 6/1983 | Sutter et al. . |
| 4,484,570 | 11/1984 | Sutter et al. . |
| 5,057,111 | 10/1991 | Park . |
| 5,151,103 | 9/1992 | Tepic et al. . |
| 5,269,784 | 12/1993 | Mast . |
| 5,501,684 | 3/1996 | Schlapfer et al. . |
| 5,520,690 | 5/1996 | Errico et al. . |

FOREIGN PATENT DOCUMENTS

| | | |
|---|---|---|
| 1329525 | 5/1994 | Canada . |
| 3027148 C2 | 5/1982 | Germany . |
| WO88/03781 | 6/1988 | WIPO . |

*Primary Examiner*—Michael Buiz
*Assistant Examiner*—Vikki Trinh
*Attorney, Agent, or Firm*—Burns, Doane, Swecker & Mathis, L.L.P.

[57] ABSTRACT

A method and a device for locking two implant elements to each other. A sleeve-shaped locking means (19) made of a polymeric material is arranged in a space adapted thereto inside the one element (3) which is placed in a corresponding hole (6) in the other element (1), alternatively between the two elements. The locking means (19) is subjected to compressive tightening, such that the resulting "pressure increase" in the means yields a locking effect on the elements (1, 3).

19 Claims, 5 Drawing Sheets

METHOD AND A DEVICE FOR IMPLANT LOCKING

FIELD OF THE INVENTION

The present invention relates generally to the locking of implant elements to each other. The invention concerns especially a method for locking two implant elements to each other, such as a plate to a bone screw passed through a plate hole, or a fixing means, such as spinal hook, on a rod-shaped strut or a rod-shaped strut end in a hole or in a sleeve, the one implant element being passed through or inserted into the other implant element and coacting parts of the implant elements being locked or fixed relative to each other by using locking means, and a device for locking two implant elements to each other, of which elements one, such a as bone screw, is passed through a hole in the other, such as a plate or a block, said one element having an end part adapted to be locked in said hole by being affected from the interior of the end part with the aid of locking means, and also a device for locking two implant elements to each other, of which elements one, such as a bone screw or a rod-shaped strut, is passed through or inserted into a hole in the other, such as plate, a spinal hook or a strut mounting, and is locked relative to said other element by using a locking means.

BACKGROUND ART

In connection with orthopedic surgery, different kinds of implant are often used. It is then a matter of fixing the implant to different kinds of bones by means of bone screws which are screwed to the bone through corresponding holes in the implant, and/or locking or fixing different implant parts to each other by means of different types of conventional locking screws which are screwed into one part to be lockingly engaged with the other part.

When using bone screws, it is well known, for locking thereof relative to the implant that is fixed by means of the bone screws, to use special locking screws which are screwed into the slit end or head or main part of the respective bone screws so as to expand the end or main part into locking engagement with the surrounding wall of the implant hole. For the purpose of achieving the necessary expansion there are arranged coacting conical surfaces on the locking and bone screws, the coacting surfaces of which, during axial relative displacement therebetween, cause a radially outwardly directed effect on said end or main part.

Typical constructions of this type are described in e.g. U.S. Pat. No. 4,484,570 and WP 88/03781.

OBJECTS OF THE INVENTION

A main object of the present invention is to provide a method for accomplishing locking of the type mentioned by way of introduction, which is generally applicable in connection with different types of implant elements.

A further object of the invention is to provide locking in a simple and effective manner.

One more object of the invention is to provide locking with an extended and well-distributed locking engagement.

A further object of the invention is to provide locking by utilizing simple means which to a smaller extent than before require specially designed elements, and in particular which do not require conical element surfaces which increase the expense.

SUMMARY OF THE INVENTION

The above-mentioned objects are achieved by a method and by devices having the features stated in the appended claims.

The invention thus is based on the knowledge that a locking effect can be obtained in an advantageous manner by using a locking means made of a material, which has the property, when subjected to compressive forces, of producing at least essentially uniformly distributed forces directed to all sides away from the material. This locking means is so arranged in connection with implant elements that are to be locked to each other that said forces produce a locking pressing action on the implant elements when the locking means in connection with locking is loaded by means of a tightenable tightening element.

The locking means is advantageously tubular or sleeve-shaped, and the loading thereof preferably occurs in an axial direction, such that said forces are obtained in a radial direction essentially perpendicular thereto. As will be immediately appreciated, it will be advantageous according to the invention to operate with generally cylindrical configurations, which means simplified production of implant elements and also a natural adaptation to existing implant constructions.

According to the invention, use is in other words made of a property of the locking means of producing, in local compression thereof, a pressure spreading distributed over the entire locking means, said pressure spreading being similar to a hydraulic effect and resulting in a most efficient and reliable locking effect.

The locking means is advantageously arranged so as to fill, to at least an essential extent, a space intended therefor and to be enclosed therein, a very small amount of compressive effect being required to obtain a "pressure increase" as required, said "pressure increase" producing the intended locking pressing action on the neighboring implant element parts. In practice, it has been found that the "tightening" that is necessary to produce the required "pressure increase" is comparatively much smaller and easier to accomplish than the locking screw tightening that has been required in the previously used constructions. This is an important advantage in the contexts that are here involved.

As a rule, the "pressure increase" is associated with at least some deformation or dimensional change of the locking means and the ensuing adaptation to the associated space, which in many cases may contribute to a better and more reliable locking effect owing to improved form-locking type engagement with neighboring implant element parts. The neighboring implant element parts can advantageously also be treated, for instance to have a rough surface of the like, to produce increased friction or form locking and, thus, improved locking engagement.

According to the invention, it is advantageous to use a locking means made of a polymeric plastic material, which preferably should have very low compressibility. A suitable material is polytetrafluoroethylene, which also has the advantage of having excellent biocompatibility.

Two main aspects of the invention may be distinguished. According to one main aspect, the locking means is arranged in the one implant element, which is adapted to be at least partially expandable outwards, said directed forces resulting in said one implant element being affected outwards into locking engagement with a surrounding second implant element either directly or via a means arranged between the implant elements, for instance a joint insert, allowing that said one implant element is selectively angularly adjustable in relation to the other implant element.

Said one implant element is especially a bone screw, the outwardly directed effect on the bone screw basically being usable in the same manner as in previous bone screw configurations with an inner locking screw. The bone screw advantageously has a cylindrical, slit main or end part with an inner cylindrical bore for receiving the locking means adapted thereto and an associated tightening element. The main or end part of the bone screw preferably has no laterally projecting end flange of such a conventional kind as is intended for engagement with the upper side of e.g. an implant plate, which is to be fixed by screwing by means of the bone screw.

According to the invention, it is, however, advantageous to fix the two implant elements to each other before locking so as to prevent relative motion therebetween in a first direction, but enabling around said direction a rotary motion of the one implant element, especially a bone screw, relative to the other implant element. For such fixing, a snap function can advantageously be utilized, using a projecting annular bead on the one expandable implant element and a matching annular groove on the other implant element or vice versa, alternatively while placing the annular bead or the annular groove on a joint insert arranged between the implant elements. The snap function is rendered possible in a simple manner owing to the possibility of easily reducing the diameter of the implant element (owing to e.g. slitting) temporarily (in any case as long as the locking means has not yet been inserted into the implant element) when inserting the implant element, allowing a space for the annular bead to pass up to and to snap into the annular groove. It will be appreciated that, if the annular bead is arranged on the implant element, it will also be slit.

A joint insert of the type indicated above may advantageously be spherical in a truncated manner, having a spherical circumferential surface and an inner cylindrical hole of a diameter corresponding to the outer diameter of the implant element which is arranged therein. A suitable slitting makes it possible to easily compress the joint insert and arrange it in a corresponding seat having a spherically designed contact surface in the other implant element.

According to said one main aspect of the invention, there is especially provided a device for locking of implant elements to each other, of which elements the one, such as a bone screw, is passed through a hole in the other, such as a plate or block, said one implant element having an end part adapted to be locked in said hole by the end part being affected from inside, said device comprising a sleeve-shaped locking means, the axial direction of which coincides with an axial direction of the end part and which is arranged in a locking space in the form of an inner annular recess in the end part to rest on a lower shoulder therein, and a tightening element adapted to be moved into tightening engagement with said one element while being engaged with the locking means so as to compress the same, the locking means, during tightening of the tightening element, exerting on the circumferential wall parts of the end part an essentially uniform pressure directed radially outwards, thereby causing the wall parts to provide a locking engagement. The locking means can also be pressed out somewhat in slits formed in the end part, which results in improved engagement between the locking means and the end part and, consequently, more reliable locking.

According to a preferred embodiment of the invention, the tightening element is a locking screw which is screwable into said end part and which has an abutment surface, for instance the underside of the screw head, for tightening engagement with the upper end of the locking means, the screw preferably being threadingly engaged with said one element below the lower shoulder and constituting an internal boundary surface of the annular recess for the locking means. The size of the ring- or sleeve-shaped recess may, as is appreciated, very well be adapted to that of the locking means, such that the locking means need be subjected but to little tightening before the recess is completely filled by the material of the locking means and a "pressure increase" causing the locking is obtained.

According to the other main aspect of the invention, the locking means is arranged between the two implant elements that are to be locked to each other, such that said directed forces cause a locking pressing action on locking surfaces, arranged opposite to each other, of the respective implant elements. In this case, use is preferably made of a sleeve-shaped locking means, which is arranged in a corresponding space which is coaxial with at least one of the two implant elements, compressive forces acting in an axial direction of the locking means and the resulting directed forces acting at least essentially perpendicularly thereto.

According to a preferred embodiment, there is provided a device for locking two implant elements to each other, of which elements the one, such as a bone screw or a rod-shaped strut, is passed through or inserted into a hole in the other, such as a plate, a spinal hook or a strut mounting, a sleeve-shaped locking means being arranged in a locking space around the first implant element, one end of the locking means resting on a shoulder on one of said two elements, and a tightening element is adapted to be moved into tightening engagement with one of said two elements while being engaged with the locking means so as to compress the same, the locking means during tightening exerting a pressure, which is directed inwards and outwards at least essentially to all sides, on neighboring parts of said one or other element, thereby locking them relative to each other. The tightening element may easily be given the shape of a sleeve-shaped nut means, which is arranged around the first element and is externally or internally threaded for engagement with a corresponding internal or external thread on the second or the first implant element.

This aspect of the invention implies radically new thinking in connection with the locking of implant elements relative to each other, by not using the locking means to accomplish a locking expansion of one of the implant elements, but instead using the capability of the actual locking means of producing, while changing dimensions to some extent, a highly well-distributed and efficient "pressurized" locking engagement with the respective implant elements. The locking configuration may be very simple in terms of construction, inexpensive and easy to handle, while the locking becomes extremely reliable.

The invention will now be described in more detail by means of embodiments with reference to the accompanying drawings.

BRIEF DESCRIPTION OF THE DRAWINGS

In the Figures, identical or corresponding elements have been given the same reference numerals.

DESCRIPTION OF EMBODIMENTS

Figures 1, 2:
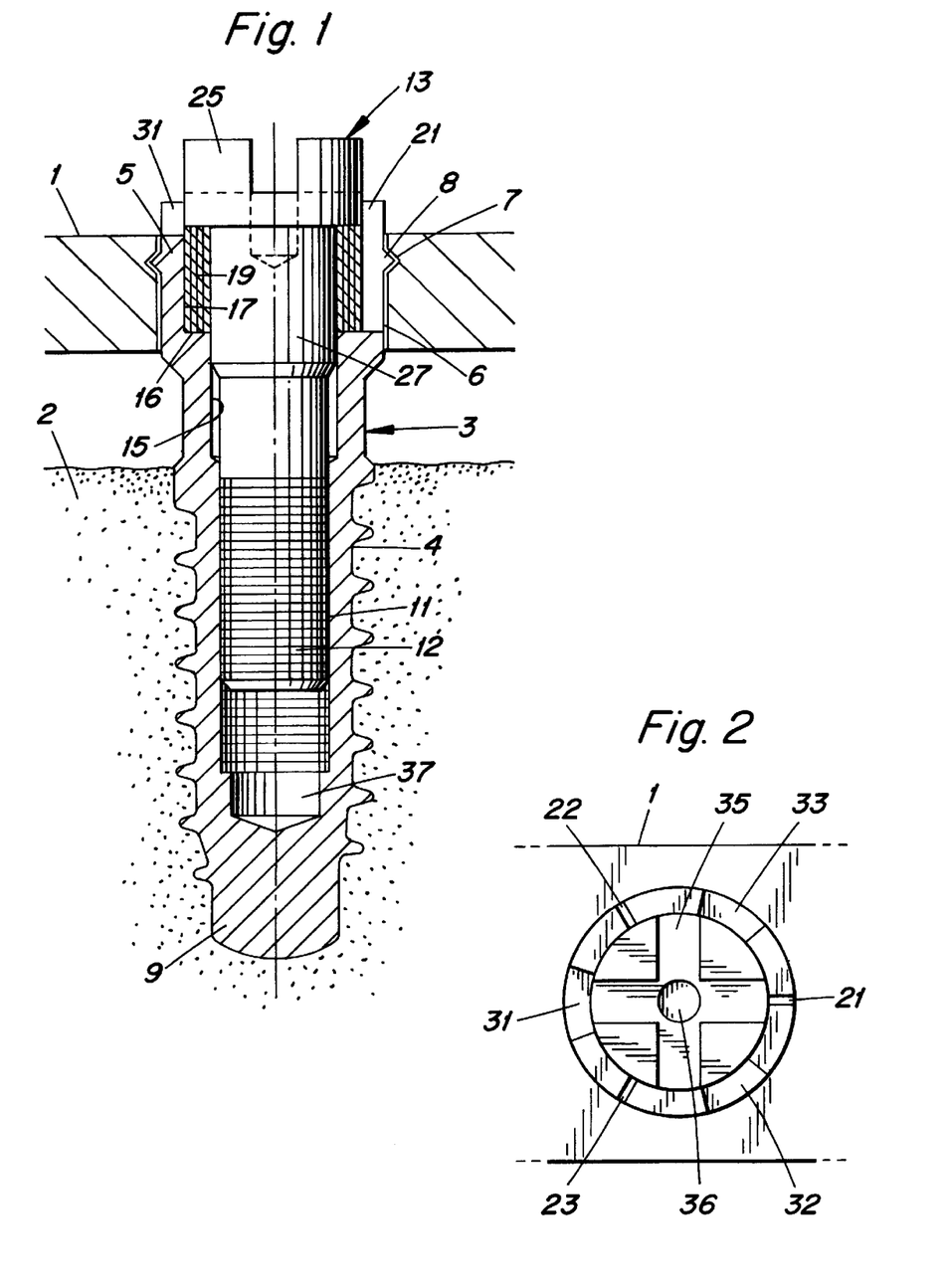
FIG. 1 is a schematic partial part-sectional view of a first embodiment of a device according to the present invention.
FIG. 2 is a schematic partial top plan view of the device in FIG. 1.

FIGS. 1 and 2 illustrate schematically an embodiment of the present invention, an elongate implant plate 1 being shown in coaction with a bone screw 3 intended to be screwed into the bone 2. The bone screw 3 has a practically fully threaded screw part 4 and a circular cylindrical end or main part 5, the diameter of which is increased in relation to the screw part and which is received with good fit in a corresponding circular cylindrical hole 6 in the plate 1. In the embodiment shown, the axial direction of the hole 6 is perpendicular to the plane of the plate 1, but it will easily be appreciated that said axial direction could be inclined in relation to the plate, resulting in angling of the bone screw 3.

The end part 5 has a height that is slightly larger than the thickness of the plate 1, the end part projecting slightly beyond the plate 1, such that the end part is easily accessible for engagement with a suitable tool for rotation of the bone screw, which will be described in more detail below. The end part 5 has no laterally projecting end flange or the like, which is normally to be found on a screw head for engagement with the element that is to be attached by means of the screw.

With a view to holding the plate 1 and the screw 3 together, thereby preventing relative motion therebetween in the axial direction of the screw in connection with the screwing of the screw into or out of the bone 2, the plate 1 is provided with an inwardly directed, essentially V-shaped circumferential annular groove 7 at the top of the wall of the hole 6, and the end part 5 is provided with a correspondingly designed projecting annular bead 8 adapted to the annular groove 7. The annular bead can be snapped into the groove 7, as will be described in more detail below. As will easily be appreciated, a fixing of this kind, which allows relative rotary motion, will permit the joint between plate and screw to be active also without the plate 1 abutting against the bone 2. The nonexistence of such abutment confers essential advantages in terms of adjustability, quicker healing and an eliminated risk of necrosis.

The bone screw 3 has an inner axial bore extending practically to the lower end 9 of the bone screw. The bore comprises a number of parts having a diameter which successively decreases downwards. The bore lower part 11, which comprises that part of the bone screw which is primarily adapted to be screwed into the bone 2 is threaded and adapted to receive the lower threaded part 12 of a tightening or locking screw 13. An intermediate part 15 of the bore has a slightly greater diameter and extends approximately up to the end part 5, where the intermediate part, via an annular shoulder 16 which is perpendicular to the axial direction of the bone screw 3, is connected with an upper bore part 17, the diameter of which is still more increased and which is adapted to receive a sleeve-shaped or tubular locking means 19 made of a polymer material, especially polytetrafluoroethylene. The locking means has an outer diameter equal to the diameter of the bore part 17 and an inner diameter equal to the diameter of the bore part 15. In other words, the locking means 19 has a radial thickness equal to the radial dimension of the annular shoulder 16. The locking means 19 has a height which is slightly smaller than the height of the bore part 17.

The end part 5 is formed with three circumferentially distributed narrow slits 21, 22, 23, extending in the longitudinal direction of the bone screw along the entire height of the bore part 17. As will easily be appreciated, these slits, although narrow, make it possible to easily mount the bone screw 3 in the plate 1 before mounting of the locking means 19 and the locking screw 13, the sections of the end part 5, which are separated by the slits 21, 22, 33, being able to spring back to the necessary extent, thereby allowing the annular bead 8 to snap into the annular groove 7.

The locking screw 13 has a head 25 with a diameter equal to the diameter of the bore part 17, such that the lower annular surface of the head can abut against the upper annular surface of the locking means 19 lowered into the bore part 17. Below the head 25, the locking screw 13 has a first unthreaded cylindrical screw part 27, the diameter of which is equal to the diameter of the bore part 15 and the length of which is slightly greater than the height of the locking means 19. As will be appreciated, the screw part 27 defines together with the wall of the bore part 17, the shoulder 16 and the lower annular surface of the screw head 25 a space which is essentially fully closed (except for the narrow slits 21, 22, 23) and which is completely filled by the essentially incompressible locking means 19. It has been found that this, together with the rest of the adjusted configuration, means that the locking screw 13 need be tightened by applying comparatively little force to achieve excellent locking and excellent stability of the joint. The evenly distributed general pressure increase obtained in said space in connection with tightening and causing the outer circumferential surface of the part 5 to be pressed against the wall of the hole 7 in an extremely efficient manner seems to be of essential significance for this purpose.

In operation, the plate 1 and the bone screw 3 are snapped together either before or in connection with the bone screw being screwed into the bone tissue 2. The bone screw 3 is rotated by means of e.g. a suitably designed tool engaging three recesses 31, 32, 33 which are distributed in the exposed end surface of the end part 5. Such rotation of the bone screw 3 may, as will be appreciated, also take place after mounting of the locking means 19 and the locking screw 13, but before tightening of the locking screw. For tightening of the locking screw 13, a recess 35 in the form of a cross and an associated central bore 36 are arranged in the exposed screw head 25 for cooperation with a correspondingly designed tightening tool.

The rotation of bone screw 3 for screwing it in or out could also take place by means of a tool which is caused to coact with the bore in the bone screw 3, in which case at least the locking screw 13 must, of course, be non-mounted or removed. For instance, the lowermost part 37 of the bore could have e.g. a square or hexagonal shape for engagement with the end of a correspondingly designed spanner inserted in the bore.

For the purpose of improving the engagement between the bone screw 3 and the bone 2, it is possible, when using a bone screw having a deep bore, for instance in accordance with the configuration in FIG. 1, to screw the bone screw into the bone with the bore unfilled in any case to such an extent that a certain inwards deformation of the threaded bone screw part becomes possible owing to the pressure from outside exerted by the bone tissue 2. When the locking screw is then screwed into the bore, a return of the bone screw to the original shape will take place, resulting in improved engagement.

As mentioned above, the shown configuration requires comparatively little tightening to provide satisfactory locking. During tightening, some of the material in the locking means—in dependence on to what small extent the material in the locking means is deformable—may be pressed into the slits 21, 22, 23, resulting in additionally improved engagement.

If additionally improved locking is desirable, one or some of the wall surface of the hole 6, the circumferential surface of the part 5, the wall surface of the bore part 17 and the circumferential surface of the part 27 may be given a suitable friction- or engagement-increasing structure, e.g. roughness, grooves, recesses etc.

Figure 3:
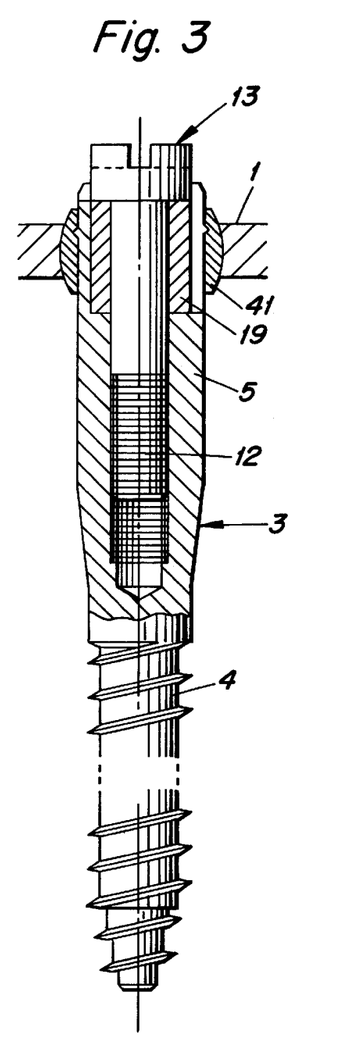
FIG. 3 is a schematic partial part-sectional view of a second embodiment of a device according to the present invention.
Figure 4:
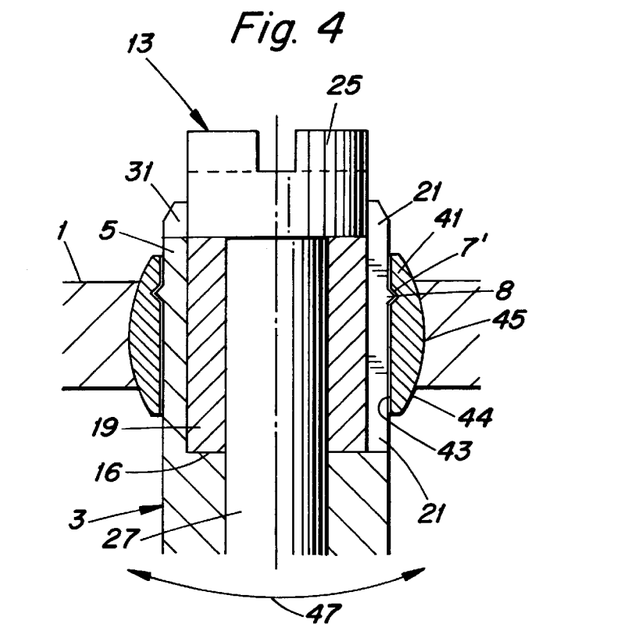
FIG. 4 illustrates on a larger scale part of the view in FIG. 3.

FIGS. 3 and 4 illustrate a further embodiment of the invention, in which the plate 1 and bone screw 3, before locking, are arranged to be able to take different relative angular positions by the end part 5 of the bone screw being rotatably fixed to the plate 1. To this end, a preferably metallic joint insert 41 is arranged between the plate 1 and the end part 5 of the bone screw. The joint insert consists of an annular element having an inner circular cylindrical wall surface 43 (corresponding to the wall surface of the hole 6 in FIG. 1) and an outer spherically designed circumferential surface 44. The hole of the plate 1 has a wall surface 45 which is spherically designed in immediate conformity with the circumferential surface 44. The annular element 41 has a height greater than the thickness of the plate 1, thereby ensuring the necessary possibility for the surface 45 to slide up and down the annular circumferential surface 44 in connection with the angling between the plate 1 and the screw 3 (as indicated by means of the double arrow 47).

In order to enable easy arrangement of the annular element 41 in the hole of the plate 1, the annular element is slit in some suitable manner (not shown in detail), whereby the annular element, during mounting, may have its diameter decreased sufficiently to allow easy insertion into the hole of the plate 1.

The end part 5 of the bone screw is fixed to the annular element 41 in the same manner as the end part 5 in FIG. 1 is fixed to the plate 1, i.e. by means of an annular groove 7' arranged at the top and an associated annular bead 8, the annular groove here being formed in the inner circular cylindrical wall surface 43 of the annular element. The locking of the joint takes place in exactly the same manner as in FIG. 1 by using a locking means 19 and a locking screw 13 inside the bone screw. The locking means 19 has in this case been given a greater height so as to extend vertically beyond the annular element 41 both upwards and downwards.

In this embodiment, the bone screw 3 is also of a slightly different design, by having an extended bored main part 5, to which a threaded homogeneous screw part 4 is connected.

Figure 5:
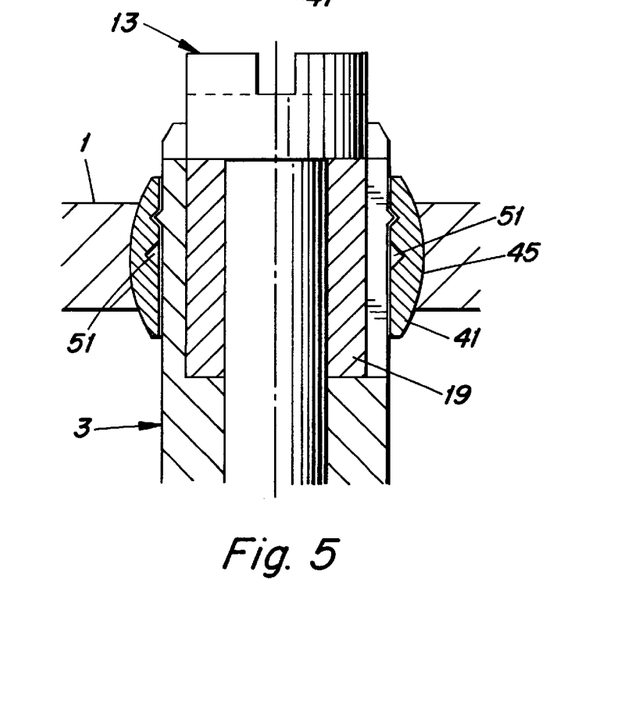
FIG. 5 is a view of the same kind as in FIG. 4, illustrating a third embodiment of a device according to the invention.

FIG. 5 illustrates a modification of the embodiment in FIGS. 3 and 4. The annular element 41 has in its inner circular cylindrical wall surface been formed with a central circumferential recess 51, which is so dimensioned that the annular element 41, when subjected to the pressing action of the end part 5 in connection with locking by tightening of the locking screws 13, tends to be deformed somewhat from the spherical circumferential shape. It has been found that the locking of the joint in this embodiment will thus be further improved.

In an embodiment according to FIG. 5 it may be advantageous to let the wall surface 45 of the plate hole have a radius of curvature which is slightly smaller than the radius of curvature of the circumferential surface 44 of the annular element 41, such that the latter, by tightening of the joint, adjusts to the curve of the wall of the hole by a minor deformation of the annular element (resulting from the arrangement of the recess 51). The deformation of the annular element means that the curve of its circumferential surface increases somewhat by a minor "folding" around the recess 51. This results in extremely good locking of the selected angular position between the plate 1 and the bone screw 3.

It will be realized that in connection with an embodiment having a central recess 51 in the annular element, it would be possible to arrange the annular bead 8 to cooperate with the recess 51, which means that the annular groove 71 can be excluded.

Figure 6:
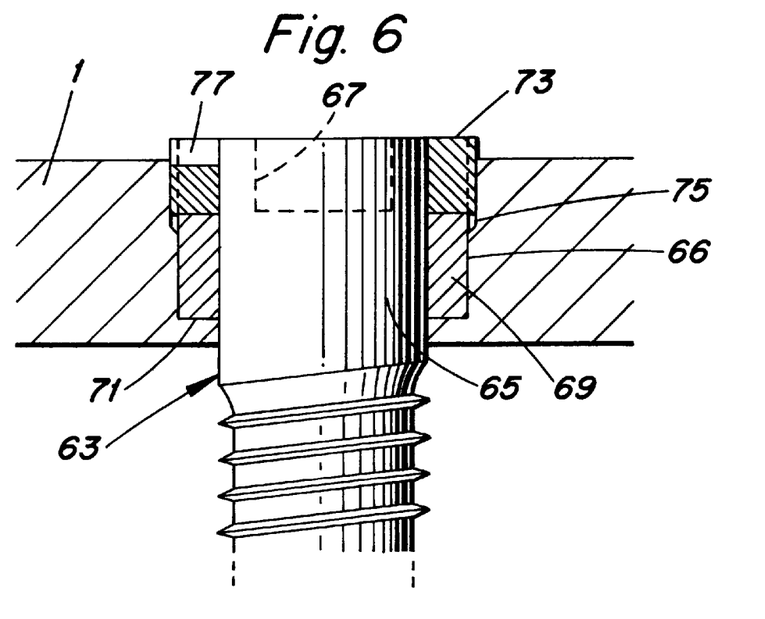
FIG. 6 is a schematic partial part-sectional view of a fourth embodiment of a device according to the invention.

FIG. 6 illustrates one more embodiment of the present invention, which differs from the embodiments described above by the fact that there is no locking force acting from inside on a bone screw 63 which is used to fix a plate 1 having a hole. Instead a sleeve-shaped locking means 69 is arranged between the end part 65 of the bone screw 63 and the corresponding hole 66 of the plate, so as to allow accomplishment of frictional engagement between the end part 5 and the locking means 69 and respectively between the locking means 69 and the wall of the hole of the plate 1. The frictional engagement is accomplished by the locking means 69 being subjected to a compressive tightening effect like in the embodiments in FIGS. 1–5.

Like before, the end part 65 of the bone screw 63 is circular cylindrical, but it has no bore. The hole 66 is also circular cylindrical with a diameter equal to that of the end part 65, increased by the radial thickness of the sleeveshaped locking means 69. The locking means 69 rests on an annular flange 71, which results in a reduction of the diameter of the hole of the plate at the lower opening thereof, the opening of the hole inside the annular flange having a diameter equal to the diameter of the end part 65 which is passed therethrough.

For tightening, i.e. compressive action on the locking means 69, use is made of a circular cylindrical ring nut 73 having an inner diameter equal to the diameter of the end part 65 and an outer diameter corresponding to the diameter of the hole 66. The ring nut is externally threaded for threaded engagement with a thread 75 in the upper part of the hole 66.

The ring or locking nut 73 can thus be screwed into the plate around the end part 65 of the bone screw after arranging the locking means 65 in its associated space which is dimensionally adjusted. The tightening of the locking nut 73, which to this end has a number of tool engagement recesses 77, 78, 79 distributed around its exposed annular end face, results in a pressure increase in the locking means, which is made of the same kind of material as the locking means in FIGS. 1–5, said pressure increase causing the desired frictional engagement. It will be appreciated that the engaging action can be improved by the circumferential surface of the end part 65 and/or the wall of the hole in the plate 1 being given a suitable structure in accordance with that discussed above in connection with the other embodiments.

It will be realized that the joint, if desired, can be assembled before screwing the bone screw 63 into a bone while using a hexagonal tool recess 67 formed in the exposed end face of the end part 65. The locking nut 73 is not tightened more than to allow the joint to stay together while the bone screw 63 can still rotate relative to the plate 1.

For the purpose of accomplishing fixing between the plate and the bone screw of the type afforded by the annular groove and the associated annular bead in the embodiments according to FIGS. 1–5, the end part of the bone screw could be provided with a radially projecting annular flange at its lower part, said annular flange being arranged on the annular flange 71, when the bone screw 63 is inserted into the hole 66 in the plate 1, i.e. before mounting of the locking means 69 and the locking nut 73. To begin with, the locking nut is fastened only to keep the joint together, while retaining the possibility of rotation of the bone screw relative to the plate.

Figure 7:
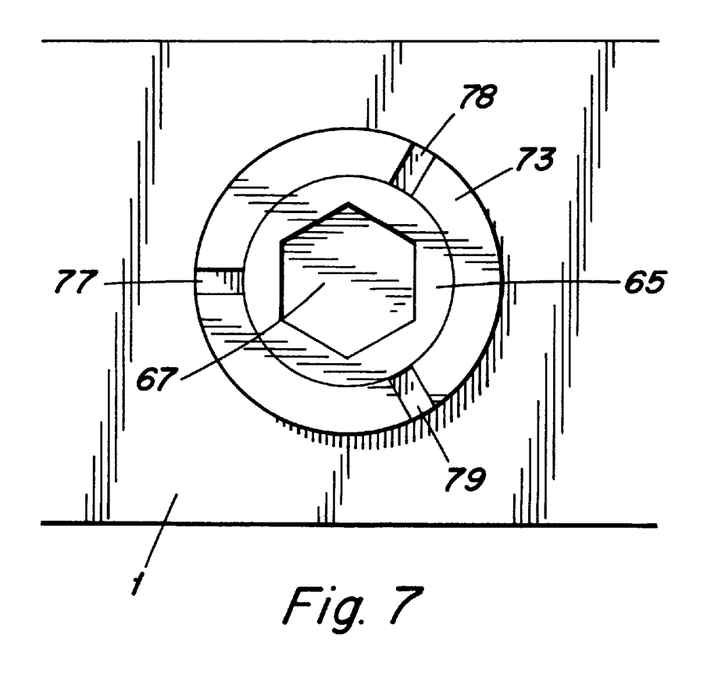
FIG. 7 is a schematic partial top plan view of the device in FIG. 6.
Figure 8:
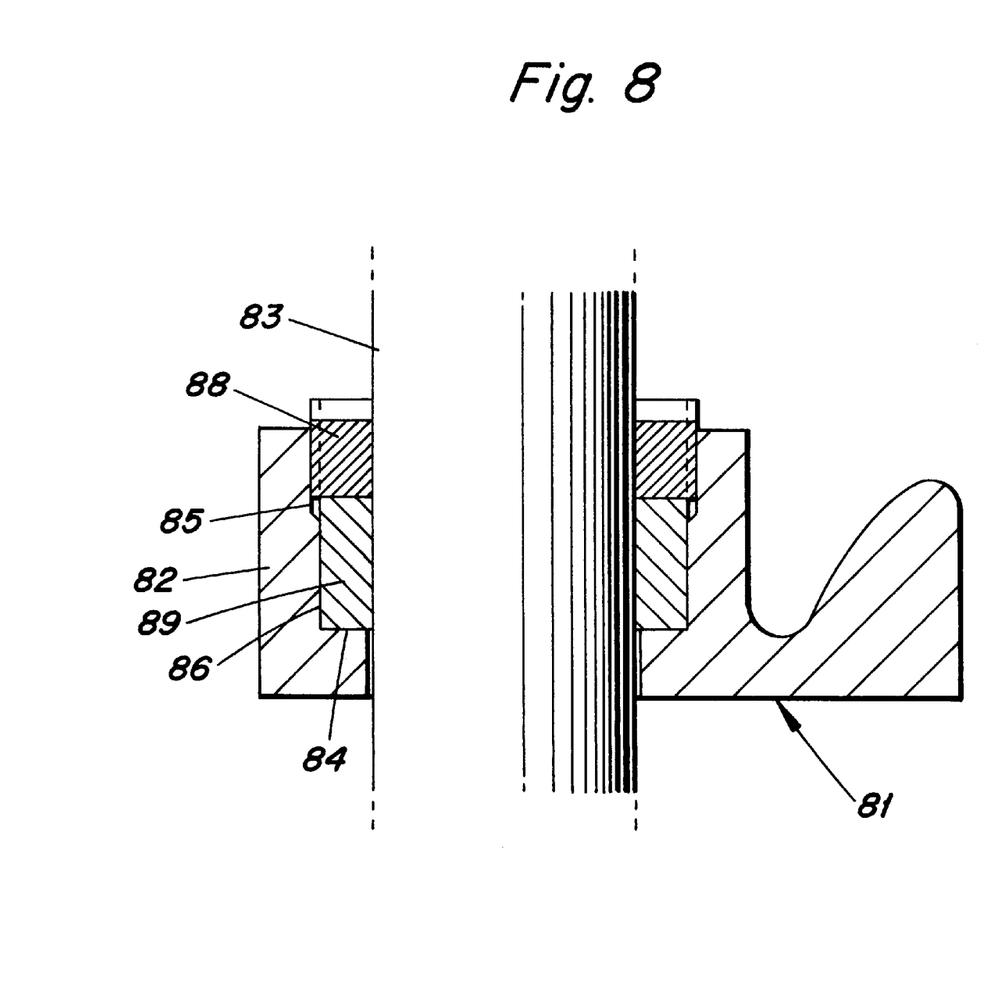
FIG. 8 is a schematic partial part-sectional view of a fifth embodiment of a device according to the invention.

FIG. 8 schematically illustrates one more embodiment of the invention, in which a fixing means 81 in the form of a spinal hook is locked onto a strut 83 by applying the same principle as in FIGS. 6–7. The strut 83 is a circular cylindrical rod and passes through a hole 86 in the fixing part 82 arranged on the hook 81 and corresponding to the plate 1 in FIG. 6. In its lower part, the hole 86 has its diameter decreased, thereby allowing the strut 83 to pass with good fit therethrough while a shoulder 84 for a locking means 89 is formed. At the top, the hole 86 has a thread 85. The locking means 89 and a locking nut 88 correspond to and function in the same manner as the locking means 69 and the locking nut 73 in FIG. 6.

As will be immediately appreciated, the spinal hook 81 can easily be displaced along the strut 83 and rotated around this to the desired engaging position, whereupon it is easily locked in the engaging position by tightening of the locking nut 88.

An advantage of the embodiment in FIG. 8 is that the strut 83 may be bent without any noticeable deterioration of the effective locking. The bend of the strut, however, should be taken into consideration when dimensioning the hole area of which the diameter is increased and the inner diameter of the locking nut. In this case, a suitable enclosure of the locking means 89 can be guaranteed by arranging metal washers on both sides of the locking means.

Figure 9:
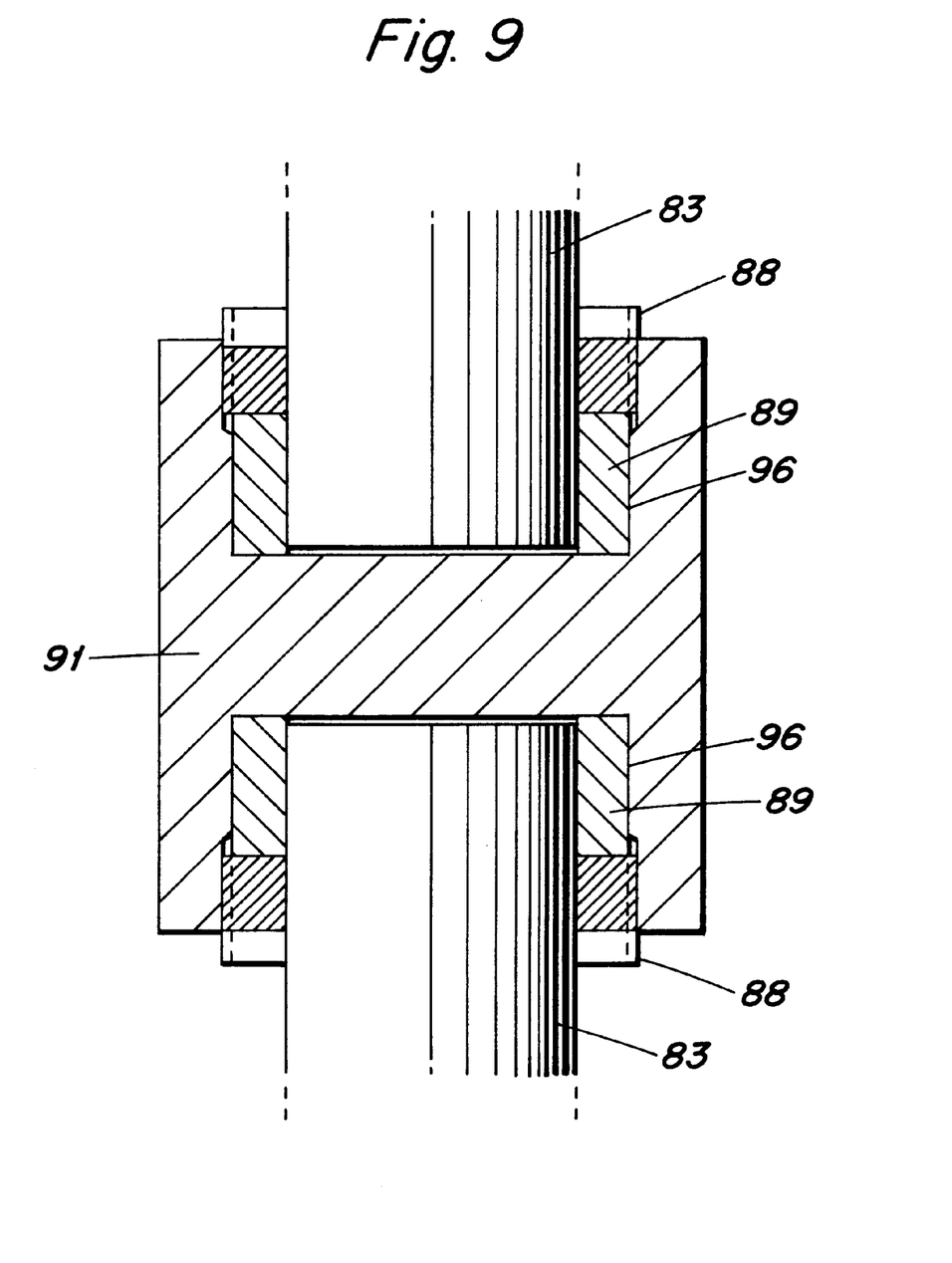
FIG. 9 is a schematic partial part-sectional view of a sixth embodiment of a device according to the invention.

Finally, FIG. 9 illustrates schematically an example of how two struts 83 can be interconnected by applying the same principle as in FIGS. 6–8. The ends of the strut are each inserted into a circular cylindrical recess 96 in a connecting body 91. Each strut end is locked in the associated recess with the aid of a locking means 89 and a locking nut 88 in the same fashion as in FIGS. 6–8.

What I claim and desire to secure by Letters Patent is:

1. An arrangement for locking implant elements to each other, comprising:
   a first implant element having an end part;
   a second implant element having a hole therein for receiving the end part, the first implant element extending through the hole;
   a sleeve-shaped lock, an axial direction of the sleeve-shaped lock coinciding with an axial direction of the end part, the sleeve-shaped lock being arranged in a locking space in the form of an inner annular recess in the end part to rest with a lower end of the sleeve-shaped lock on a lower shoulder of the locking space; and
   a tightening element screwed into tightening engagement with the first implant element while being engaged with the sleeve-shaped lock so as to compress the sleeve-shaped lock, the tightening element and the sleeve-shaped lock being arranged to cooperate such that the sleeve-shaped lock, during tightening of the tightening element, exerts a pressure directed at least essentially to all sides on circumferential wall parts of the end part to cause the wall parts to engage the second implant element and lock the first implant element and the second implant element together.

2. An arrangement as claimed in claim 1, wherein the tightening element is a locking screw which is screwable into the end part and which has an abutment surface for tightening engagement with an upper end of the sleeve shaped lock.

3. An arrangement as claimed in claim 2, wherein the end part is rotatable within but axially non-displaceably connected to the second implant element.

4. An arrangement as claimed in claim 2, wherein the locking screw is threadingly engaged with the first implant element below the lower shoulder and define an internal boundary surface of the annular recess for the sleeve-shaped lock.

5. An arrangement as claimed in claim 1, wherein the end part is rotatable within but axially non-displaceably connected to the second implant element.

6. An arrangement as claimed in claim 5, wherein the end part is connected to the second implant element by a projecting annular bead on one of the end part and the second implant element and a matching annular groove on one of the second implant element and the end part, respectively.

7. An arrangement as claimed in claim 5, wherein the end part is connected in an angularly adjustable manner to the second implant element by an intermediate joint insert.

8. An arrangement as claimed in claim 7, wherein the end part is connected to the second implant element by a projecting annular bead on one of the end part and the second implant element and a matching annular groove on one of the second implant element and the end part, respectively.

9. An arrangement as claimed in claim 1, wherein the end part is connected in an angularly adjustable manner to the second implant element by an intermediate joint insert.

10. An arrangement as claimed in claim 9, wherein the end part is connected to the second implant element by a projecting annular bead on one of the end part and the second implant element and a matching annular groove on one of the second implant element and the end part, respectively.

11. An arrangement as claimed in claim 9, wherein the end part is connected to the second implant element by a projecting annular bead on one of the intermediate joint insert and the second implant element and a matching annular groove on one of the second implant element and the intermediate joint insert, respectively.

12. An arrangement as claimed in claim 1, wherein the sleeve-shaped lock is made of a polymeric plastic material having very low compressibility.

13. An arrangement as claimed in claim 12, wherein the sleeve-shaped lock is made of polytetrafluoroethylene.

14. An arrangement as claimed in claim 12, wherein the sleeve-shaped lock is arranged so that after application of the tightening element, the sleeve-shaped lock is substantially completely enclosed.

15. An arrangement as claimed in claim 1, wherein the sleeve-shaped lock is arranged so that after application of the tightening element, the sleeve-shaped lock is substantially completely enclosed.

16. An arrangement as claimed in claim 1, wherein one or more surfaces of at least one of the first implant element and the second implant element are provided with engagement increasing structure.

17. An arrangement for locking implant elements to each other, comprising:

a first implant element and a second implant element, the second implant element having a hole therein and the first implant element extending into the hole;

a sleeve-shaped lock arranged in a locking space around the first implant element in the hole area and inside the surrounding second implant element, one end of the sleeve-shaped lock resting on a shoulder on one of the first implant element and the second implant element; and a tightening element screwed into tightening engagement with one of the first implant element and the second implant element while being compressively engaged with the sleeve-shaped lock, the tightening element and the sleeve-shaped lock cooperating such that the sleeve-shaped lock, during tightening of the tightening element, exerts pressure directed inwards and outwards at least essentially to all sides on neighboring parts of the one of the first implant element and the second implant element, thereby locking the first implant element and the second implant element relative to each other, the tightening element being a sleeve-shaped nut arranged around the first implant element and being threaded for engagement with a corresponding thread on the one of the one of the first implant element and the second implant element.

18. An arrangement as claimed in claim 17, wherein the sleeve-shaped lock is made of a polymeric plastic material having very low compressibility.

19. An arrangement as claimed in claim 16, wherein the sleeve-shaped lock is made of polytetrafluoroethylene.

* * * * *